Figure 1:
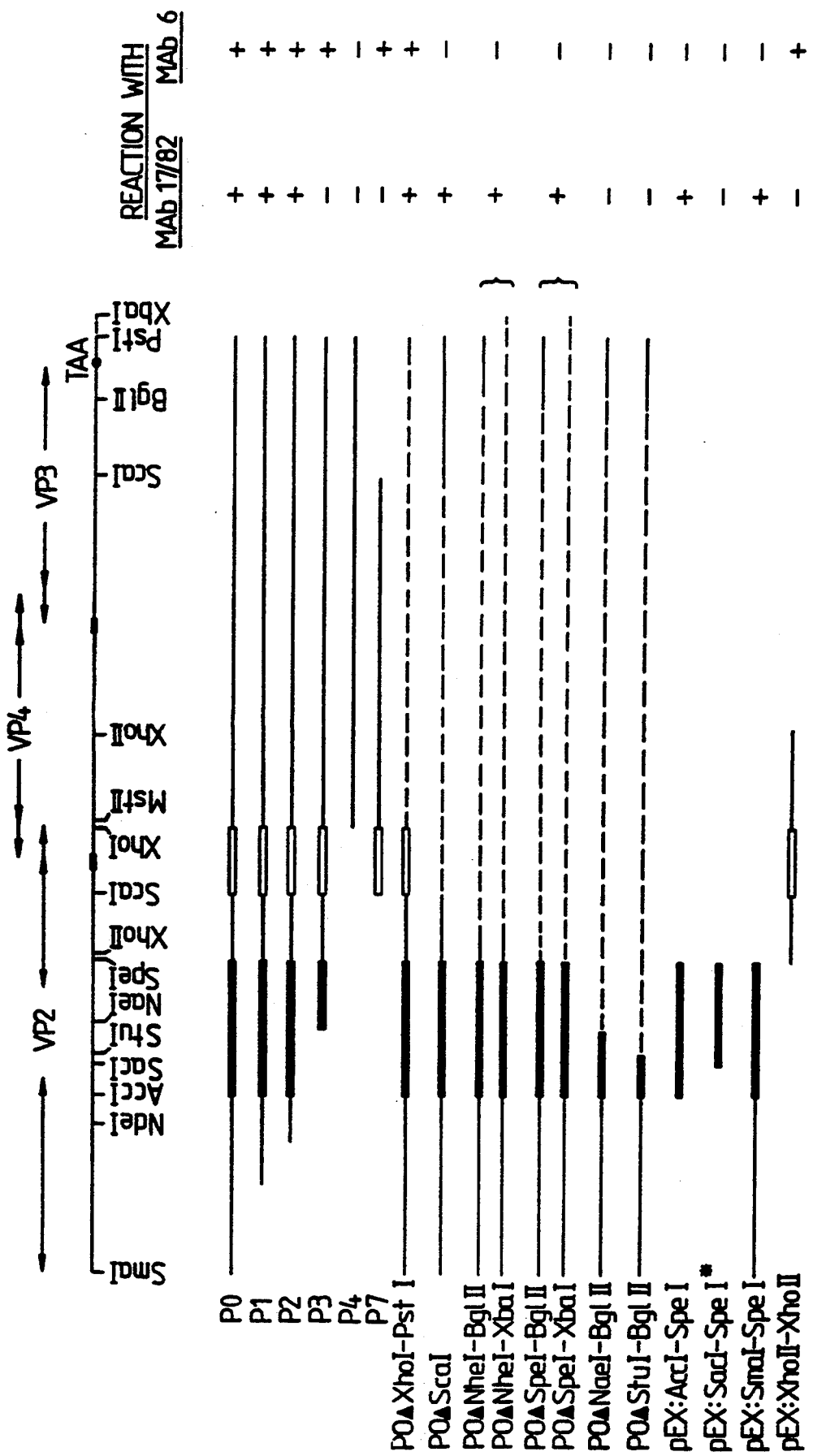

United States Patent [19]

Azad et al.

[11] Patent Number: 5,350,575

[45] Date of Patent: Sep. 27, 1994

[54] IBDV VP2 EPITOPE RECOGNIZED BY VIRUS NEUTRALIZING AND PROTECTIVE MONOCLONAL ANTIBODIES

[75] Inventors: Ahmed A. Azad; Mittur N. Jagadish; Kevin J. Fahey, all of Melbourne, Australia

[73] Assignee: Commonwealth Scientific and Industrial Research Organisation, Campbell, Australia

[21] Appl. No.: 52,289

[22] Filed: Apr. 26, 1993

Related U.S. Application Data

[63] Continuation of Ser. No. 457,744, Feb. 26, 1990, abandoned.

[30] Foreign Application Priority Data

Jun. 26, 1987 [AU] Australia ............................ PI2727/87

[51] Int. Cl.$^5$ ...................... A61K 39/12; C12N 15/09; C12N 1/21; C07K 15/12
[52] U.S. Cl. ............................... 424/192.1; 424/204.1; 435/69.3; 435/69.7; 435/240.2; 435/252.3; 435/320.1; 536/23.4; 536/23.72; 530/350; 530/403
[58] Field of Search ............... 435/69.3, 69.7, 240.2, 435/252.3, 320.1, 188; 424/88, 89, 94.3; 536/23.4, 23.72; 530/350, 403

[56] References Cited

FOREIGN PATENT DOCUMENTS

8502545  6/1985  World Int. Prop. O. ... A61K 39/12
8607060 12/1986  World Int. Prop. O. ... C07H 21/04

OTHER PUBLICATIONS

Azad et al., (1985), Virology, 143:35–44.
Fahey et al., (1985), J. Gen. Virol., 66:2693–2702.
Fahey et al., (1985b), J. Gen. Virol., 66:1479–1488.
Hudson et al., (1986), Nucl. Acids. Res., 14(12):5001–12.

Primary Examiner—Kay K. Kim
Attorney, Agent, or Firm—Bacon & Thomas

[57] ABSTRACT

A recombinant DNA molecule comprising a nucleotide sequence coding for a conformational epitope of the VP2 polypeptide of IBDV. In particular, a DNA molecule comprising a sequence which substantially corresponds to the AccI-SpeI fragment, and optionally the ScaI-XhoI fragment, of the IBDV genome segment coding for the VP2 polypeptide. Synthetic peptides or polypeptides, including fused polypeptides, prepared by expression of host cells containing these DNA molecules are also disclosed, as well as compositions for stimulating an immune response against IBDV comprising at least one such synthetic peptide or polypeptides.

17 Claims, 2 Drawing Sheets

IBDV VP2 EPITOPE RECOGNIZED BY VIRUS NEUTRALIZING AND PROTECTIVE MONOCLONAL ANTIBODIES

This application is a Continuation of application Ser. No. 07/457,744, filed Feb. 26, 1990, now abandoned.

Infectious bursal disease virus (IBDV), a member of the newly recognised Birnaviridae family, causes severe immunodeficiency in young chickens by destroying the precursors of antibody-producing B cells in the bursa of Fabricius, one of the two major immunological organs of birds.

Birnaviruses contain four polypeptides which are termed VP1 (90–100 kD), VP2 (41–54 kD), VP3 (32–35 kD) and VP 4 (24–29 kD) (Dobos et. al., 1979). VP1, VP3 and VP4 of IBDV have molecular weights of approximately 90 kD, 32 kD and 28 kD respectively (Dobos et. al., 1979; Fahey et. al., 1985a). Vp2 of the Australian stain of IBDV (Firth, 1974) has calculated MW of ca. 52 kD from sequencing studies (Hudson et. al., 1986) but migrates as two bands of ca. 41 kD and 37 kD (Fahey et. al., 1985a) on Laemmli gels (Laemmli, 1970). The reduced apparent molecular weight might be due to the highly hydrophobic character of the protein (see FIG. 2). Peptide mapping studies (Neil McKern, unpublished data) show that the viral 41 kD and 37 kD polypeptides have a precursor-product relationship, and are therefore termed VP2a and VP2b.

The large genomic segment of infectious bursal disease virus encodes a polyprotein in which the viral polypeptides are present in the following order: N-VP2-VP4-VP3-C. Expression in E. coli of the large segment results in the processing of the polyprotein. The expression product reacts with a virus neutralizing and protective monoclonal antibody that recognises a conformational epitope on the surface of the virus. Deletion of different regions of the large genomic segment followed by expression in E.coli shows that the conformational epitope recognised by this monoclonal antibody is present within VP2 (International patent Application No. PCT/AU86/00156).

Native VP2 isolated from the virus is precipitated by chicken antibodies raised against IBDV that neutralize the virus and passively protects chickens from IBDV infection. When injected into chickens, the native VP2 produces virus neutralizing antibodies in both rabbits and chickens. The latter passively protect chickens from IBDV infection (Fahey et. al., manuscript submitted). Recombinant VP2, produced in E.coli, also produces virus-neutralizing and protective antibodies in chickens. These results clearly establish VP2 as a major host-protective immunogen of IBDV.

The present invention derives from the identification of a conformational epitope within VP2 that is recognised by a number of virus-neutralizing monoclonal antibodies (VN MAbs) raised against the virus.

According to the present invention there is provided a recombinant DNA molecule comprising a nucleotide sequence coding for a conformational epitope of the VP2 polypeptide of IBDV. Expression of this molecule leads to the expression of a peptide that is recognised by virus neutralizing monoclonal antibodies raised against the IBD virus.

In particular, the present invention provides a recombinant DNA molecule, comprising a nucleotide sequence corresponding to the AccI-SpeI fragment, optionally together with the ScaI-XhoI fragment, of the IBDV genome segment coding for the VP2 polypeptide.

It will be appreciated that the nucleotide sequence of this aspect of the invention may be obtained from natural, synthetic or semi-synthetic sources, or by manipulation of the natural material; furthermore, this nucleotide sequence may be a naturally-occurring sequence, or it may be related by mutation, including single or multiple base substitutions, deletions, insertions and inversions, to such a naturally-occurring sequence, provided always that the DNA molecule comprising such a sequence is capable of being expressed as a conformational epitope of the VP2 polypeptide of IBDV.

The nucleotide sequence may have expression control sequences positioned adjacent to it, such control sequences being derived either from IBDV nucleic acid or from a heterologous source.

This invention also provides a recombinant DNA molecule comprising an expression control sequence having promoter sequences and initiator sequences, and a nucleotide sequence coding for a conformational epitope of the VP2 polypeptide of IBDV.

In yet another aspect, the invention provides a recombinant DNA cloning vehicle capable of expressing a conformational epitope of the VP2 polypeptide of IBDV, comprising an expression control sequence having promoter sequences and initiator sequences, and a nucleotide sequence coding for a conformational epitope of the VP2 polypeptide of IBDV.

In a further aspect, there is provided a host cell containing a recombinant DNA cloning vehicle and/or a recombinant DNA molecule as described above.

In yet further aspects, there is provided polypeptides displaying IBDV antigenicity which can be produced by a host cell transformed or infected with a recombinant DNA cloning vehicle as described above. Such expressed polypeptides may comprise the polypeptides encoded by the AccI-SpeI fragment, and optionally the ScaI-XhoI fragment, of the IBDV genome segment coding for the VP2 polypeptide.

The present invention also extends to synthetic peptides or polypeptides displaying the antigenicity of a conformational epitope of the VP2 polypeptide of IBDV.

As used herein, the term "synthetic" means that the peptides or polypeptides have been produced by chemical and/or biological means, such as by means of chemical synthesis or by recombinant DNA techniques leading to biological synthesis. Such polypeptides can, of course, be obtained by direct expression by a host-cell of a correctly processed and folded protein, or by cleavage of a fused polypeptide produced by a host cell and separation of the desired polypeptide from additional polypeptide coded for by the DNA of the host cell or cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure.

It will be appreciated that polypeptides displaying antigenicity of a conformational epitope of the VP2 polypeptide of IBDV will have utility in serological diagnosis, and in the preparation of single or multivalent vaccines against IBDV by methods well known in the art of vaccine manufacture. Further details of such vaccines, and of methods of use thereof, as well as of quantitative and qualitative assays, are disclosed in International Patent Specification No. PCT/AU84/00256.

EXAMPLE 1

The following detailed description relates to the identification of a conformational epitope within VP2 that is recognised by virus-neutralizing monoclonal antibodies.

In the accompanying drawings:

FIG. 1 shows the identification of antigenic regions recognised by MAb 17/82 and MAb 6. Proteins from clones in which different regions of VP2 were deleted were isolated under non-denaturing conditions, spotted onto nitrocellulose filter and probed with the monoclonal antibodies. The closed boxes indicate the region of VP2 that is recognised by MAb 17/82. The 145 amino acid peptide encoded by the AccI-SpeI fragment is the minimum region of VP2 required from reaction with Mab 17/82, and with MAbs 3/1, 32/3, 39A, 9/6, 33/10 and 44/18. The open boxes indicate the 68 amino acid peptide that is recognised by MAb6.

Figure 2:
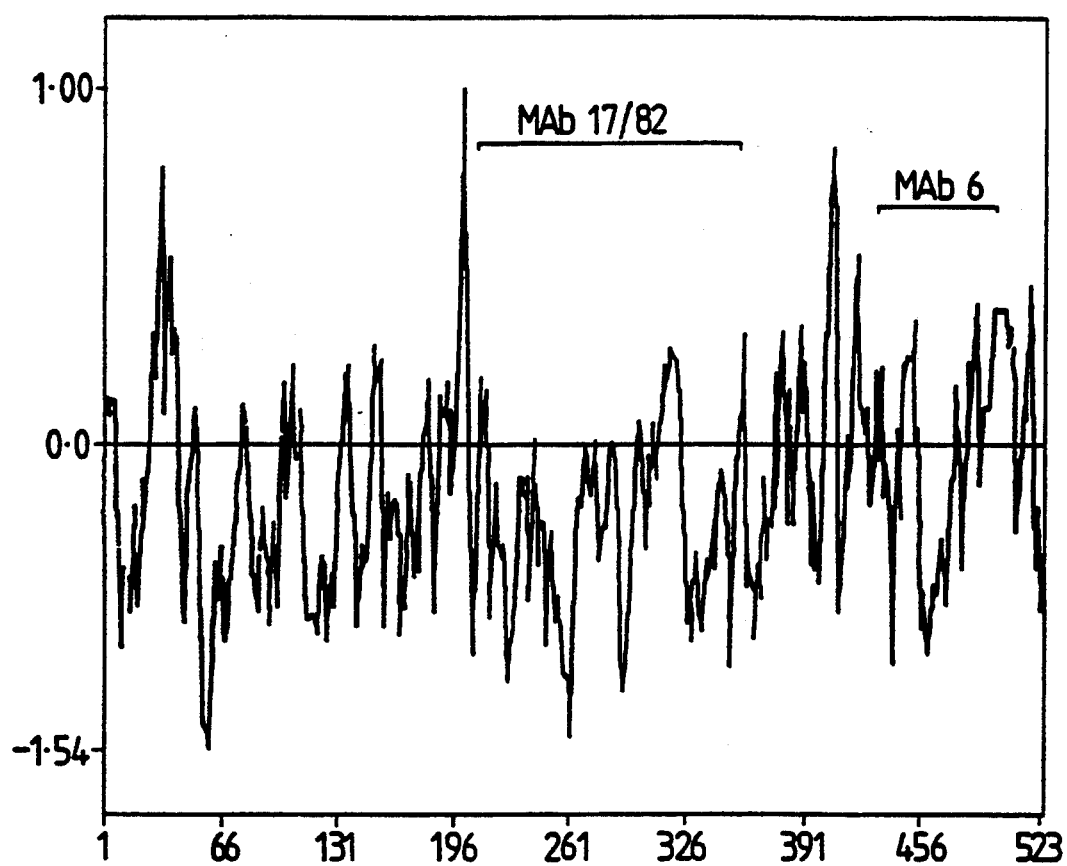

FIG. 2 shows the hydrophilicity profile over VP2 encoded by clone POΔ XhoI-PstI. Hydrophilicity calculations were smoothed by averaging over hexapeptide segments as described by Hopp and Woods (1981).

MATERIALS AND METHODS

Production of Monoclonal Antibodies against IBDV

BALB/C mice were immunised with whole virus and the spleen cells fused with SP-2 or NS-1 myeloma cells. The hybridomas were plated out in multiwell trays and supernates screened by immunodotting of whole virus on nitrocellulose sheets. Positive wells were cloned three times at limiting dilution and screened by virus neutralization, Western blotting of whole virus and immunoprecipitation of native and denatured viral proteins.

Specificity of the anti-IBDV monoclonal antibodies

The monoclonal antibodies were reacted with viral proteins that had been separated by SDS-PAGE and transferred to nitrocellulose paper according to the method described by Fahey et. al. (1985a). The IgG fractions of the tissue culture supernates of the monoclonal antibody cultures were purified by affinity chromatography and injected intraperitoneally into 3-day-old chickens, which were then challenged intraocularly with 100 CID50 of virulent virus 6 hours later. The chickens were post-mortemed 3 days later and the serum and bursa of Fabricius assessed by ELISA for residual monoclonal antibody activity and IBD viral antigen (Fahey, et. al., 1985b). In order to assess the ability of the MAbs to immunoprecipitate native VP2a/2b, Protein A-Sepharose (Pharmacia) was activated with rabbit IgG anti-mouse Ig and mouse monoclonal antibody, prior to being blocked with normal rabbit serum and normal mouse serum. The activated Sepharose was then reacted with the viral protein, washed and analysed on SDS-PAGE gels. The precipitated viral protein was detected with a mixture of monoclonal antibodies that Western blotted VP2a/2b and VP3. The in vitro virus neutralizing activity of the monoclones was assessed using strain GT101 of IBDV, that had been adapted to tissue culture, and grown in chick kidney cells (Fahey et. al., 1985b), while an additive ELISA was used to assess the specificity of the MAbs (Friguet et. al., 1983).

Virus Strain

The IBDV strain (002-73) used in these studies is an Australian field isolate (Firth, 1974). The major structural difference with European and North American strains seems to be the fact that the major 41 kD structural protein (VP2a) is substantially cleaved to a 37 kD species (VP2b) in the Australian strain. The strain GT101 of IBDV was adapted from the field strain, to grow in tissue culture.

Expression Vectors

The pEX1-3 vectors (Stanley and Luzio, 1984) and *E. coli* pop 2136 were obtained from Dr. Keith Stanley. pUR290-292 vectors (Ruther and Muller-Hill, 1983), and pCQV2 vector (Queen, 1983) were received from Drs. B. Muller-Hill and Cary Queen, respectively. The pPL vector was obtained from Pharmacia.

Recombinant clones used to define processing and antigenicity

The large RNA segment of the IBDV genome contains a long open reading frame in which the viral proteins encoded by the large segment are arranged in the following order: N-VP2-VP4-VP3-C (Hudson, et. al., 1986). Clones which contains the VP3 coding region are designated Dn. Expression clones D6 and D1, which encode the entire VP3 or a segment of it, respectively, have been described before (Azad, et. al., 1986).

Clones which contain the VP3 coding region and sequences upstream of it are designated Pn (precursor to VP3). The strategy used for the cloning of the IBDV genome (Azad, et. al., 1985) gave rise to a cDNA library consisting of overlapping fragments covering the entire genome. A cDNA fragment equivalent to the large RNA segment could therefore be constructed by joining smaller overlapping fragments from the cDNA library (Azad, et. al., 1985) through common restriction sites as described previously (Hudson, et. al., 1986). clone P1 was constructed by joining cDNA clones D6 and L6 (Azad, et. al., 1985) at a common ApaI site into pUR vectors, thus expressing the major part of VP2 together with VP4 and VP3 (residues 125–1011) fused to β-galactosidase (see FIG. 1). Clone PO was constructed in pEX3 vector by extending the P1 insert with the insert of clone G6 (Azad, et. al., 1985) to express essentially the entire IBDV large segment coding region (residues 5–1011) fused to β-galactosidase.

For the construction of clones P2 to P4, the insert from clone PO was excised with SmaI and PstI. For the construction of clones P2-P4, the PO insert was progressively deleted from the 5' end at unique restriction sites and, after appropriate end filled-in reactions, these variously sized fragments were blunt-end ligated into HpaI-cut pPL vector. To construct clone P7, a ScaI-Sca I fragment was excised from clone PO and religated into the SmaI site of the expression vector pEX1. In all these clones the N-terminus of the IBDV polypeptide was fused in-phase to a 7 KD fragment of the N protein.

Clones derived from PO in which deletions were carried out between two restriction sites downstream of the site of fusion are designated POΔ x→y, where x and y are restriction sites. In instances where fragments from within the VP2-encoding region were cloned directly in pEX vectors the clones are designated as pEX x→y. All these vectors produced β-galactosidase fusion proteins.

Clone pEX SacI-SpeI was constructed by removing a 1kb SacI fragment and religating the plasmid. This kept the IBDV protein in phase with the N-terminal portion of β-galactosidase but resulted in the deletion of the C-terminal third of the enzyme.

The exact regions of the IBDV large RNA segment present in the different clones are shown in FIG. 1. The host-vector systems and growth and induction conditions are summarised in Table 1.

The amounts of fusion proteins produced ranged from ca. 20% of the total *E. coli* protein in clones where the IBDV polypeptide was preceded by 110 kD β-galactosidase, to ca. 5% of the total protein in clones which had a 7 kD N-terminal fusion. The amount of unfused protein of the expected size produced in clone D2 (FIG. 2) was less than 1% of the total protein. The 100 Kd β-galactosidase fusion proteins formed insoluble inclusion bodies which were quantitatively pelleted at 12,000 rpm. The 7 kD N-protein fusion polypeptides, on the other hand, remained in the supernatant when spun at 12,000 rpm.

TABLE 1

Summary of Host-Vector Systems, and Growth and Induction Conditions.

| Clone | Vector | E. coli Host | IBDV protein fused to | Growth temp. | Induction |
|---|---|---|---|---|---|
| P0 | | | 110 kD | 32° | 42°, 2 hr |
| P0 Δx→y | pEX | pop2136 | β-galacto- | | |
| pEX x→y | | | sidase | | |
| P2-P4 | pPL | pop2136 | 7 kD λN protein | 32° | 42°, 2 hr |
| D2 | pCQV2 | RR1 | Unfused | 32° | 42°, 2 hr. |
| D6 | | | | | |
| D1 | pUR | RR1 | 110 kD | 37° | 1.5M IPTG |
| P1 | | JM101 | β-galacto-sidase. | | 37°, 4 hr |

Recombinant DNA techniques

Isolation of plasmid DNA and restriction fragments, molecular hybridization, *E. coli* transformation and other general molecular biology techniques were performed as described in a previous paper (Azad, et. al., 1985).

Analysis of expressed proteins

Immunoassays of expressed proteins in recombinant colonies and characterization of isolated proteins by immunodot assays, PAGE and Western blotting were carried out as described earlier (Azad, et. al., 1986).

RESULTS

To define the minimum region within VP2 recognised by a number of virus-neutralizing monoclonal antibodies, the VP2-encoding region of VP2 was progressively deleted from both the 5' and 3' ends at specific restriction sites (FIG. 1) and ligated into *E. coli* expression vectors ensuring that the IBDV polypeptide was in phase with the N-terminal fusion protein. The proteins expressed in *E. coli* were analysed under non-denaturing conditions by reaction with different Mays. Progressive deletions of the VP2-encoding region from the 5' end show that the loss of the sequence 5' to the AccI site does not affect reaction with the virus neutralizing Mays (FIG. 1). A further deletion to the SacI site completely abolishes this reaction. Thus the N-terminus of the reactive site lies 3' to the AccI site and 5' to or spanning the SacI site. Similar progressive deletions from the 3' end show that deletions 3' to the SpeI site do not affect reaction with MAb 17/82, but the reaction is abolished by a further deletion to the NaeI site. Thus the C-terminus of the reactive peptide is encoded by a sequence that lies 5' to the SpeI site and 3' to or spaning the NaeI site. Thus, the conformational epitope recognised by the virus neutralizing MAb 17/82 is contained with the 145 amino acid polypeptide encoded by the AccI-SpeI fragment (closed box, FIG. 1). This is also the minimum region required for reaction with Mays 39A, 3/1, 32/3, 9/6, 33/10 and 44/18. The expression product of this fragment (clone pEX AccI-SpeI) reacts very strongly with MAb 17/82 (FIG. 1). Since there are no half cystines present within this region of VP2 (Hudson, et. al., 1986b) disulfide bonds are not expected to be important for this conformational determinant. The region of VP2 reacting with MAb 17/82 is extremely hydrophobic with a small hydrophilic region present at each terminus (FIG. 2). The N-terminal region is encoded by the AccI-SacI fragment, and the C-terminal region by the NaeI-SpeI fragment. Since 5' deletion from AccI→SacI and 3' deletion from SpeI→NaeI completely abolish reaction with MAb 17/82, the two hydrophilic regions are important determinants within the conformational epitope recognised by MAb 17/82. Similar deletion expression studies show that the epitope recognised by MAb 6 is encoded by a 204 b.p. ScaI-XhoI fragment present at the C-terminus of VP2 (FIG. 1). These results are consistent with previous observations (Fahey, et. al., manuscript in preparation) that MAb 6 Western blots VP2a (41 kD) but not VP2b (37 kD) derived from it.

Properties of Monoclonal Antibodies

Western blotting of whole IBDV separated the monoclonal antibodies into four groups:
i: Mays 1/1 and 17/80 which reacted with VP3.
ii: MAb 6/1 which reacted with VP2a, but not VP2b.
iii: Mays 9/6, 33/10 and 44/18 which react with denatured VP2a and VP2b.
and iv: Mays 3/1, 17/82, 32/3 and 39A which did not Western blot any of the viral protein.

Six of these Mays (3/1, 9/6, 17/82, 32/3, 33/10 and 39A) neutralised IBDV in vitro, and 17/82 and 39A also passively protected susceptible chickens from infection (others still being tested). MAb 44/18, which resembled 9/6 and 33/10 by Western blotting, did not neutralize the virus. Similarly MAbs 1/1, 6/1 and 17/80 did not neutralize the virus in vitro and 17/80 did not passively protect susceptible chickens.

MAbs 9/6, 3/1, 32/3, 17/82 and 39A specifically immunoprecipitated native VP2a and VP2b, and almost completely block the ability of immune chicken serum to react with IBDV in the ELISA.

The additive ELISA showed that MAbs 3/1, 9/6, 17/82, 32/3, 33/10 and 39A react with epitopes on the virus which results in them competing with each other, even sterically, for the same binding sites. The non-neutralizing, anti-VP2a/2b MAb, 44/18, only partially competed with the other virus neutralizing MAbs.

These anti-IBDV MAbs have been used to detect specific chicken antibody in serum and quantitate viral antigen in infected bursae, thereby demonstrating their potential value as diagnostic or quantitative reagents. Immune chicken serum can be quantitated in a competitive ELISA using the virus neutralizing MAbs, while these same MAbs can quantitate viral antigen in diagnostic samples and batches of viral or recombinant protein, prior to their formulation as vaccines. MAb 6/1, 9/6 and 33/10 have been particularly useful in quantitating the total amount of specific protein in denatured/solubilised preparations of virus or recombinant viral protein.

injected intramuscularly at several sites into three 6-week-old specific pathogen free (SPF) chickens. The chickens were bled from the wing vein at regular intervals and injected with the same amount of fusion protein emulsified in Freunds Incomplete Adjuvant at 10 weeks of age. The chickens were again bled and the antibody responses measured by ELISA and by a virus neutralisation assay. A group of 3 control chickens were treated in exactly the same manner, but received a fusion protein containing an irrelevant clone.

Passive protection of susceptable chickens

Sera from chicken 7642 which had the highest titre of virus neutralising antibody was pooled and separated into 19S and 7S globulins by chromatography on a S300 (Pharmacia) column using 0.01M phosphate buffer, pH7.6. The two fractions were concentrated using an XM100A membrane (Diaflow) and sterile filtered through a 0.22$\mu$ membrane (Millipore).

Groups of eight 3-day-old chickens were injected intraperitoneally (i.p.) with 1 ml of globulin solution

TABLE 2

Specificity and biological activity of monoclonal antibodies to IBDV.

| MAb | Immunodot* | Western Blot | Specificity Immunoprecipation** | In vitro virus neutralization | Biological Activity In vivo passive protection |
|---|---|---|---|---|---|
| 1/1 & 17/80 | ++ (+++) | VP3 | | Negative | Negative |
| 6/1 | + (+++) | VP2a | | Negative | |
| 9/6 & 33/10 | ++++ (++++) | VP2a/2b | VP2a/2b | Positive | |
| 44/18 | ++++ (++++) | VP2a/2b | | Negative | |
| 3/1 17/82 32/3 & 39A | ++++ (−) | Neg. | VP2a/2b | Positive | Positive |

*Immunodot on whole virus(s) (denatured virus).
**Immunoprecipitation of native VP2a2/b protein isolated from whole virus.

EXAMPLE 2

The following detailed description indicates the presence of a critical protective epitope within VP2 that induces virus neutralising antibodies in chickens which passively protect susceptible chickens from infection with Infectious Bursal Disease Virus (IBDV).

In the accompanying data, Table 3 shows the response of three 6-week-old SPF chickens to 1 mg of protein from clone POΔXhOI-PstI (FIG. 1) emulsified in adjuvant and injected at days 0 and 28. Virus neutralising and ELISA responses were determined for the experimental group and a group of control chickens injected similarly with an irrelevant construct.

Table 4 shows the absence of IBDV antigen in the bursa of Fabricius of the majority of chickens passively protected with IgG or IgM antibody from chicken 7242 (Table 3), following challenge with virulent IBDV. Viral antigen in the bursa and residual passive antibody in the paired serum from each chicken was assayed by ELISA, 3 days after the challenge infection.

MATERIAL AND METHODS

Immunisation of Chickens with Recombinant VP2

Insoluble fusion protein of clone POΔXhoI-PstI (2 mg/ml) expressed in the pEX vector was emulsified in an equal volume of Freunds Complete Adjuvant and then challenged 24 hrs later with 100 chick infectious doses ($CID_{50}$) of virulent IBDV (strain 002/73). A group of control chickens that received an i.p. injection of phosphate buffered saline (PBS) were similarly challenged.

Three days after challenge the chickens were exsanguinated and the bursa of Fabricius removed. The bursae was sonicated in 1 ml of PBS to a homogeneous suspension. The paired serum and bursal homogenate from each chicken was assayed by ELISA for residual antibody and viral antigen respectively.

RESULTS

Response of SPF chickens to recombinant VP2

All three chickens injected with protein from clone POΔ XhoI-PstI as a pEX fusion protein, produced virus neutralising and ELISA antibodies by 3 weeks post-inoculation. A second dose of the fusion protein increased the titres further, particularly the antibody detected by the ELISA (Table 3). The titres of antibody in the control chickens were uniformly negative by the virus neutralisation assay and near background levels by ELISA. Chickens 7642 produced the highest, longest persisting titres of antibody and sera from this chicken were pooled and used in subsequent passive protection studies.

Passive protection of susceptible chickens with chicken antibodies to recombinant VP2

Both the 19S globulin (IgM) and 7S globulin (IgG) fractions of serum from chickens 7642 passively protected 4-day-old chickens from infection with virulent IBDV. Six of the 8 chickens that received IgG and 7 of the 8 that received IgM were completely protected. All control chickens were uniformly susceptible. The lower titres of residual ELISA antibody in the chickens receiving IgG antibody may account for the susceptibility of the two chickens in this group that did succumb following challenge. Nevertheless a total of 13 of the 16 chickens receiving fractions of serum containing antibodies to recombinant VP2 were protected against the virulent challenge infection.

TABLE 3

Reciprocal titre of virus neutralising (VN) and ELISA antibody in serum from chickens injected with recombinant VP2 (Expt. 1) or irrelevant protein (control).

| Chicken No. | VN | ELISA | VN | ELISA | VN | ELISA |
|---|---|---|---|---|---|---|
| | | | Weeks Post-inoculation | | | |
| Expt. 1 | 0 | | 3 | | 4 | |
| 7641 | <20 | <50 | 320 | 200 | 640 | 600 |
| 7642 | <20 | <50 | 80 | 400 | 2560 | 800 |
| 7646 | <20 | <50 | 40 | 150 | 320 | 300 |
| | 6 | | 8 | | 11 | |
| 7641 | 1024 | 300 | 160 | 1200 | 320 | 2400 |
| 7642 | 5120 | 1400 | 5120 | 1600 | 3200 | 4800 |
| 7646 | — | 400 | 80 | 1200 | 80 | 500 |
| Control | 0 | | 3 | | 4 | |
| 7643 | <20 | <50 | <20 | <50 | <20 | 150 |
| 7644 | <20 | <50 | <20 | <50 | <20 | <50 |
| 7645 | <20 | <50 | <20 | <50 | <20 | <50 |
| | 6 | | 8 | | 11 | |
| 7643 | <20 | 100 | <20 | 75 | <20 | 200 |
| 7644 | <20 | <50 | <20 | <50 | <20 | <50 |
| 7645 | <20 | 100 | <20 | 50 | <20 | 150 |

TABLE 4

Passive protection of susceptible chickens with IgG and IgM antibody from chicken 7642.

| 7642 IgG | | | 7642 IgM | | | PBS | | |
|---|---|---|---|---|---|---|---|---|
| Chick No.* | AG | AB | Chick No.* | AG | AB | Chick No.* | AG | AB |
| 1 | <1 | 60 | 9 | <1 | 120 | 17 | >128 | <4 |
| 2 | <1 | 40 | 10 | <1 | 80 | 18 | >128 | <4 |
| 3 | <1 | 30 | 11 | <1 | 120 | 19 | >128 | <4 |
| 4 | <1 | 60 | 12 | <1 | 80 | 20 | >128 | <4 |
| 5 | <1 | 60 | 13 | 24 | 80 | 21 | >128 | <4 |
| 6 | 64 | 60 | 14 | <1 | 120 | 22 | >128 | <4 |
| 7 | >128 | 60 | 15 | <1 | 120 | 23 | >128 | <4 |
| 8 | <1 | 60 | 16 | <1 | 120 | 24 | >128 | <4 |

*The chickens were challenged with IBDV (002/73) and viral antigen (AG) in bursae and residual antibody (AB) in serum are expressed as reciprocal ELISA titres.

REFERENCES

1. Azad, A. A., Barrett, S. A. and Fehey, K. J. (1985). The characterization and molecular cloning of the double-stranded RNA genome of an Australian strain of infectious bursal disease virus. *Virology.* 143: 35–44.
2. Azad, A. A., Fahey, K., Barrett, S., Erney, K. and Hudson, P. (1986). Expression in *Escherichia coli* of cDNA fragments encoding the gene for the host-protective antigen of infectious bursal disease virus. *Virology* 149: 190–198.
3. Dobos, P., Hill, B. J., Hallett, R., Kells, D. T. C., Becht, H. and Tenninges, D. (1979). Biophysical and biochemical characterization of five animal viruses with bisegmented double-stranded RNA genomes. *J. Virol.* 32: 593–605.
4. Fahey, K. J., O'Donnell, I. J. and Azad, A. A. (1985a). Characterization by Western Blotting of the immunogens of infectious bursal disease virus. *J. Gen. Virol.* 66: 1479–1488.
5. Fahey, K. J., O'Donnell, I. J. and Bagust, T. J. (1985b). Antibody to the 32 kD structural protein of infectious bursal disease virus neutralizes viral infectivity in vitro and confers protection on young chickens. *J. Gen. Virol.* 66: 2693–2702.
6. Firth, G. A. (1974). Occurrence of an infectious bursal syndrome within an Australian poultry flock. *Aust. Vet. J.* 50: 128–130.
7. Friguet, B., Djavadi-Ohaniance, L., Pages, J., Bussard, A. and Goldberg, M. (1983). *J. Immun. Methods* 60: 315–358.
8. Hoop, T. P. and Woods, K. R. (1981). Prediction of protein antigenic determinants from amino acid sequences. *Proc.Natl.Acd. Sci. USA.* 78: 3824–3828.
9. Hudson, P. J., McKern, N. M., Power, B. E. and Azad, A. A. (1986). Genomic structure of the large RNA segment of infectious bursal disease virus. *Nuc..Acids Res.* 14: 5001–5012.
10. King, P. V. and Blakesley, R. W. (1986). Optimizing DNA ligations for transformation. *Focus* (BRL Technical Bulletin) 8.1: 1–3.
11. Laemmli, U. K. (1970). Cleavage of structural proteins during the assembly of the head of Bacteriophage T4. *Nature* 227: 680–685.
12. Queen, C. (1983). A vector that uses phage signals for efficient synthesis of proteins in *Escherichia coli*. *J.Mol.Appl.Gen.* 2: 1–10.
13. Ruther, V. and Muller-Hill, B. (1983). Easy identification of cDNA clones. *EMBO J.* 2: 1791–1794.
14. Stanley, K. K. and Luzio, J. P. (1984). Construction of a new family of high efficiency bacterial expression vectors: identification of cDNA clones coding for human liver proteins. *EMBO J* 3: 1429–1434.

We claim:

1. A recombinant DNA molecule consisting essentially of a nucleotide sequence coding for a non-full length fragment of VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide.

2. A recombinant DNA molecule according to claim 1, wherein said nucleotide sequence is operatively linked to an expression control sequence.

3. A recombinant DNA cloning vehicle or vector capable of expressing a non-full length fragment of the VP2 polypeptide of IBDV including a conformational epitope of the VP2 polypeptide, said cloning vehicle or vector having inserted therein a nucleotide sequence according to claim 1, said sequence being operatively linked to an expression control sequence.

4. A host cell containing a recombinant DNA molecule according to claim 2.

5. A host cell containing a recombinant DNA cloning vehicle or vector according to claim 3.

6. A synthetic peptide or polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide.

7. A fused polypeptide comprising a polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide as the C-terminal sequence, and an additional non-IBDV polypeptide encoded by an expression vehicle or vector as the N-terminal sequence fused thereto.

8. A method of preparing a synthetic peptide or polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide, which comprises expression of a host cell according to claim 4, and recovery of the synthetic peptide or polypeptide or fused polypeptide.

9. A method of preparing a synthetic peptide or polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide, which comprises expression of a host cell according to claim 5, and recovery of the synthetic peptide or polypeptide or fused polypeptide.

10. A method of preparing a fused polypeptide comprising a polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide as the C-terminal sequence, and an additional non-IBDV polypeptide encoded by an expression vehicle or vector as the N-terminal sequence fused thereto, which comprises expression of a host cell according to claim 4, and recovery of the synthetic peptide or polypeptide or fused polypeptide.

11. A method of preparing a fused polypeptide comprising a polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide as the C-terminal sequence, and an additional non-IBDV polypeptide encoded by an expression vehicle or vector as the N-terminal sequence fused thereto, which comprises expression of a host cell according to claim 5, and recovery of the synthetic peptide or polypeptide or fused polypeptide.

12. A composition for stimulating an immune response against IBDV, which comprises at least one synthetic peptide or polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment, of the IBDV genome segment coding for the VP2 polypeptide, together with a pharmaceutically acceptable carrier therefor.

13. A composition according to claim 12 which further comprises an adjuvant.

14. A composition for stimulating an immune response against IBDV, which comprises a fused polypeptide comprising a polypeptide having the antigenicity of a non-full length fragment of the VP2 polypeptide of IBDV including a conformational epitope of the VP2 polypeptide, said conformational epitope encoded by the AccI-SpeI fragment, optionally together with the ScaI-XhoI fragment of the IBDV genome segment coding for the VP2 polypeptide as the C-terminal sequence, and an additional non-IBDV polypeptide encoded by an expression vehicle or vector as the N-terminal sequence fused thereto, together with a pharmaceutically acceptable carrier therefor.

15. A composition according to claim 14, further comprising an adjuvant.

16. A method of stimulating an immune response against IBDV in poultry, which comprises administering to said poultry a composition according to claim 12.

17. A method of stimulating an immune response against IBDV in poultry, which comprises administering to said poultry a composition according to claim 14.

* * * * *